United States Patent [19]

Shimada et al.

[11] Patent Number: 5,470,555
[45] Date of Patent: Nov. 28, 1995

[54] PROCESS FOR PURIFICATION OF GASEOUS ORGANOMETALLIC COMPOUND

[75] Inventors: Takashi Shimada; Keiichi Iwata; Masako Yasuda, all of Hiratsuka, Japan

[73] Assignee: Japan Pionics Co., Ltd., Tokyo, Japan

[21] Appl. No.: 202,701

[22] Filed: Feb. 23, 1994

Related U.S. Application Data

[63] Continuation of Ser. No. 904,166, Jun. 25, 1992, abandoned.

[30] Foreign Application Priority Data

Jul. 17, 1991 [JP] Japan .................................. 3-268121
Jul. 17, 1991 [JP] Japan .................................. 3-268122

[51] Int. Cl.$^6$ .......................... B01D 53/46; C07F 19/00; C23C 16/16; C23C 16/18
[52] U.S. Cl. ............... 423/219; 423/210; 556/1; 260/665 R
[58] Field of Search .................... 423/210, 219; 556/1; 562/899; 260/665 R

[56] References Cited

U.S. PATENT DOCUMENTS

| | | | |
|---|---|---|---|
| 2,144,497 | 1/1939 | La Pelle | 423/219 |
| 2,351,167 | 6/1944 | Ware | 423/219 |
| 3,852,406 | 12/1974 | Krauss et al. | 423/219 |
| 4,034,062 | 7/1977 | Krueger | 423/219 |
| 4,683,125 | 7/1987 | Yusa | 423/220 |
| 4,713,224 | 12/1987 | Tamhankar et al. | 423/219 |
| 4,772,296 | 9/1988 | Potts | 55/67 |
| 4,800,189 | 1/1989 | Eschwey et al. | 423/219 |
| 5,019,364 | 5/1991 | Kitahara et al. | 423/210 |

FOREIGN PATENT DOCUMENTS

| | | |
|---|---|---|
| 0240270 | 10/1987 | European Pat. Off. . |
| 0361386 | 4/1990 | European Pat. Off. . |
| 50-06440 | 3/1975 | Japan .................................. 423/219 |
| 3-12303 | 1/1991 | Japan . |
| 2254860 | 10/1992 | United Kingdom .................... 423/210 |
| 9117285 | 11/1991 | WIPO . |

OTHER PUBLICATIONS

Patent Abstracts of Japan, vol. 15, No. 128 (C–818)(4656) Mar. 28, 1991 of JP–A–30 12 303, (Japan Pionics) Jan. 21, 1991.

Primary Examiner—Ferris Lander
Assistant Examiner—Peter T. DiMauro
Attorney, Agent, or Firm—Frishauf, Holtz, Goodman, Langer & Chick

[57] ABSTRACT

There is disclosed a process for purification a gaseous organometallic compound containing impurities by bringing the compound into contact with a catalyst comprising a copper or nickel component as the essential ingredient to remove oxygen contained in the compound. The above-mentioned process is capable removal of oxygen in an organometallic compound as low as 0.1 ppm and further to a ultralow concentration of 0.01 ppm, which removal has heretofore been impossible, and thereby the production of a ultrapure organometallic compound has been made possible.

14 Claims, No Drawings

PROCESS FOR PURIFICATION OF GASEOUS ORGANOMETALLIC COMPOUND

This application is a Continuation, of application Ser. No. 07/904,166, field Jun. 25, 1992, now abandoned.

BACKGROUND OF THE INVENTION

1. Field of the Invention

The present invention relates to a process for the purification of a gaseous organometallic compound. More particularly, it pertains to a process for the purification of a gaseous organometallic compound which process is capable of removing oxygen contained as an impurity in the gaseous organometallic compound down to a ultralow concentration.

Much importance is attached to the organometallic compounds each derived from a Ib, IIb or IIIb element of the Periodic Table, which compounds are typified by diethylzinc, trimethylaluminum, trimethylgallium, trimethylindium, dimethylgold acetylacetonato, etc., as they are used as raw materials for producing compound semiconductors such as zinc selenide (ZnSe), gallium-aresenic compound (GaAs) and indium-phosphorus compound (InP) and as wiring fabrication materials. In addition, such compounds as biscyclopentadienylmagnesium, tetramethyltin and dimethyltellurium increase their usage year by year as raw materials for doping. With the advanced performance of semiconductors in recent years, the above-mentioned raw materials are required to be ultralow in the content of impurities. 2. Description of the Related Art With respect to the method for feeding an organometallic compound to be used during the production of a semiconductor, although diethylzinc is sometimes fed from a cylinder filled in with the gas thereof diluted with hydrogen or the like to 1% or less, there are usually available a method in which an organometallic compound is placed in a container such as a bottle one end of which is open to the air, the container is immersed in a thermostat and adjusted to an appropriate temperature and the resultant vapor of the organometallic compound is fed to a reactor while the flow rate of the vapor is controlled with a mass flow controller or the like, or a method in which an organometallic compound placed in a bubbler is subjected to bubbling by $H_2$, $N_2$ or He and the resultant vapor of the compound is fed to a reactor.

An organometallic compound usually contains oxygen, moisture and the like as impurities, of which moisture is removable by means of a dehumidifying agent such as zeolite.

The oxygen content in an organometallic compound is usually 10 ppm or less but in recent years there is available in the market the compound having a relatively low content of oxygen as low as 0.1 to 0.5 ppm.

Recently it has been made possible to highly purify arsine, phosphine and hydrogen selenide that are simultaneously used with an organometallic compound during the production of a compound semiconductor, enabling to lower an oxygen contained therein as an impurity to 0.01 ppm or less (refer to Japanese Patent Applicaiton Laid-Open No. 12303/1991, etc.). Under such circumstance the organometallic compound to be used therewith having an oxygen content of 0.01 ppm or less is eagerly desired.

In addition since the aforementioned organometallic compounds are sometimes contaminated with an impurity such as air mixing therein in the course of being fed to a semiconductor fabrication apparatus, for example, at the time of connecting a bottle, switching a pipeline or the like, it is desirable that the impurities be finally eliminated immediately before feeding to the apparatus. The demand for a highly purified organometallic compound continues to increase year by year. Nevertheless there is hardly found a publicly known technique capable of efficiently removing oxygen contained in organometallic compounds.

In view of the aforesaid situation intensive research was concentrated by the present inventors on a process for efficiently removing oxygen contained in organometallic compounds down to a ultralow level. As a result it has been discovered that the oxygen contained therein can be removed as low as 0.1 ppm and further 0.01 ppm by bringing an organometallic compound into contact with a specific catalyst comprising copper or nickel as the essential ingredient. The present invention has been accomplished on the basis of the above-mentioned finding and information.

SUMMARY OF THE INVENTION

It is an object of the present invention to develop a process for efficiently removing oxygen contained as an impurity in an organometallic compound down to a ultralow concentration.

It is another object of the present invention to develop a process for producing a highly purified organometallic compound in which impurities such as oxygen are almost completely removed.

Specifically the present invention provides a process for purifying a gaseous organometallic compound containing impurities which process is characterized in that the oxygen contained therein as an impurity is removed by bringing the compound into contact with a specific catalyst comprising copper or nickel as the essential ingredient.

DESCRIPTION OF PREFERRED EMBODIMENTS

The present invention is concerned with a process for purifying an organometallic compound which comprises removing oxygen contained in the compound alone or diluted with hydrogen (hydrogen gas-based) or an inert gas such as nitrogen or argon (inert gas-based).

The organometallic compound to be the object of the process according to the present invention includes the organometallic compound which is in the form of gas at ordinary temperature or vaporizable by bubbling with a diluting gas, by heating or the like and typified by dimethylzinc, diethylzinc, dimethylcadminum, diethylcadminum, dimethylmercury, trimethylaluminum, triethylaluminum, diisobutylaluminum hydride, dimethylaluminum hydride, trimethoxyaluminum [$Al(OCH_3)_3$], dimethylaluminum monochloride, trimethylgallium, triethylgallium, triethoxygallium [$Ga(OC_2H_5)_3$], trimethylindium, triethylindium, dimethylgold acetyacetonato [$Au(CH_3)_2(C_5H_7O_2)$], bishexafluoroacetyl acetonato copper [$Cu(HFA)_2$] (wherein HFA is hexafluoroacetyl acetonato group). Most of the aforementioned compounds are each a compound of an element belonging to the group Ib, IIb or IIIb of the Periodic Table and a saturated or unsaturated hydrocarbon with or without partial substitution by hydrogen, a halogen, an alkoxy group, an acetyl group or the like. Other examples include biscyclopentadienylmagnesium [$Mg(C_5H_4)_2$], tetramethyltin, trimethylarsenic, trimethylphosphorous, dimethylselenium, diethylselenium, dimethyltellurium and pentacarbonyliron [$Fe(CO)_5$], which are derived from an element belonging to the group IIa, IVb, Vb, VIb or VIII of the Periodic Table.

As mentioned above, the organometallic compound to be the object of the process according to the present invention is gaseous at ordinary temperature and contains oxygen as an impurity.

The catalyst to be used in the present invention comprises a copper or nickel component as the essential ingredient, which is enumerated by metallic copper, copper compound liable to be reduced such as copper oxide, metallic nickel and nickel compound liable to be reduced such as nickel oxide. The catalyst may contain a small amount of chromium, iron or cobalt as a metallic component other than copper or nickel.

The above-mentioned catalyst may be used alone or with a carrier, but for the purpose of enhancing the efficiency of contact between gas and the surface of copper or nickel component, it is usually used in the state of being deposited on a carrier.

There are available various methods for producing a copper oxide, including a method in which an alkali such as caustic soda, caustic potash, sodium carbonate or ammonia is added to the nitrate, sulfate, chloride or an organic acid salt each of copper to precipitate an intermediate of an oxide thereof, followed by calcining the precipitate.

The calcined product thus obtained is usually molded by means of extrusion molding, tabletting molding or the like, and the molding is used as such or after being crushed into the product of a suitable size. The molding may be carried out by dry process or wet process, in which a small amount of water, a lubricant or the like can be used.

The catalyst to be used in the present invention can be prepared by the above-stated process or selected from a commercially available copper catalyst product in different forms insofar as the copper component in the form of reduced or oxidized copper is finely dispersed and enhanced in the surface area thereof, that is, the efficiency of contact between the gas and the catalyst.

There are available some methods for depositing a nickel component on a carrier, including, for example, a method wherein a carrier powder such as the powder of diatomaceous earth, alumina, silica-alumina, aluminosilicate or calcium silicate is dispersed in aqueous solution of an nickel salt, an alkali is added to the dispersion to deposit the nickel component on the carrier powder followed by filtration to form a cake, which is then washed with water as necessary, dried at 20° to 150° C., calcined at 300° C. and the calcined product is crushed; and a method wherein an inorganic nickel salt such as $NiCO_3$, $Ni(OH)_2$, $Ni(NO_3)_2$ or an organic nickel salt such as $NiC_2O_4$, $Ni(CH_3COO)_2$ is calcined, the calcined product is crushed, mixed with heat resistant cement and the mixture is calcined.

The calcined product thus obtained is usually molded by means of extrusion molding, tabletting molding or the like, and the molding is used as such as after being crushed into the product of a suitable size. The molding can be carried out by dry process or wet process, in which a small a small amount of water, a lubricant or the like can be used.

The nickel-based catalyst to be used in the present invention can be selected from commercially available nickel catalyst products in different forms such as steam modification catalyst tradenamed "C11-2-03" (NiO-cement), "C-11- 2-06" (NiO-refractory), "C11-2" (Ni-calcium aluminate), "C11-9" (Ni-alumina); hydrogenation catalyst tradenamed "C46-7" (Ni-diatomaceous earth), "C46-8" (Ni-silica), C36 (Ni—Co—Cr-alumina); gasification catalyst tradenamed XC99 (NiO); hydrogenation modification catalyst tradenamed C20-7 (Ni—Mo-alumina), each being produced by Toyo CCI Corporation; gasifying modification catalyst tradenemed N-174 (NiO); gasification catalyst tradenamed N-185 (NiO), each being produced by JGC Corporation.

In summary, any form of the nickel catalyst can be used in the present invention inasmuch as the nickel component in the form of reduced or oxidized nickel is finely dispersed and enhanced in the surface area thereof as well as the efficiency of contact between the gas and the catalyst.

The above-described catalyst to be used in the process according to the present invention which comprises a copper or nickel component as the essential ingredient has a specific surface area usually in the range of 10 to 300 $m^2/g$, preferably 30 to 250 $m^2/g$ as measured by BET method.

The content of a copper or nickel component is 5 to 95% by weight, preferably 20 to 95% by weight as expressed in terms of metal content. A content of a copper or nickel component lower than 5% by weight deteriorate deoxidation performance, whereas a content higher than 95% by weight involves the possibility of decreasing the catalytic activity due to sintering caused in the course of reduction by hydrogen.

In order to activate the foregoing catalyst material, reduction by hydrogen is usually carried out. The aforesaid reduction by hydrogen can be put into practice by passing a gas mixture of hydrogen and nitrogen at 350° C. or lower and at a space linear velocity (LV) of 5 cm/sec., approximately. In the case of reduction, however, care should be exercised not to allow the temperature to suddenly rise by reason of exothermic reaction.

The purification of an organometallic compound is accomplished ordinarily by passing, as a raw material, the gaseous organometallic compound containing the impurities through a purification cylinder packed therein with a catalyst comprising reduced copper or nickel as the essential ingredient. By the contact between the organometallic compound and the aforementioned catalyst, the oxygen contained therein as an impurity is removed.

The concentration of oxygen in the organometallic compound to be purified (crude organometallic compound) is not specifically limited, but it is usually 100 ppm or lower. The concentration thereof higher than 100 ppm requires, as the case may be, a means for removing heat since heat generation increases with an increase in oxygen concentration.

The length of the catalyst to be packed in the purification cylinder is usually in the range of 50 to 1500 mm judged from the practical point of view. The length thereof of less than 50 mm causes a possibility of decreasing the oxygen removal efficiency, while the length more than 1500 mm causes a fear of excessively increasing the pressure loss through the packed catalyst.

The space linear velocity (LV) of the crude organometallic compound during purification varies depending on the oxygen concentration in the compound, operation conditions and the like and therefore, can not be generally defined. However, it is usually 100 cm/sec or less, preferably 30 cm/sec or less.

The temperature of the crude organometallic compound brought into contact with the catalyst, which signifies the temperature of the above compound in the form of gas when fed at the inlet of the purification cylinder is not higher than 200° C., and usually it can be ordinary temperature, dispensing with heating or cooling.

The pressure of the gas fed to the cylinder is not specifically limited but can be equal to or lower or higher than ordinary pressure, usually 20 kg/cm² or lower, preferably 0.1 to 10 kg/cm² abs.

A small amount of moisture, even if contained in the crude organometallic compound, does not particularly exert an evil influence on the deoxidation performance of the catalyst. Moreover, the use of a catalyst carrier or the like enables the removal of moisture as well as oxygen depending upon type of the carrier to be used.

It is possible to combine the process of removing oxygen with a catalyst in the present invention with a process of removing moisture by the use of a synthetic zeolite, etc. according to the demand. The above combined processes remove moisture as well as oxygen almost completely and enable the production of a highly purified organometallic compound.

According to the present invention, it has been made possible to remove oxygen contained in an organometallic compound down to a ultralow concentration of 0.1 ppm or less and further 0.01 ppm or less and therefore to obtain a ultrapure organometallic compound substantially free from oxygen.

In the following, the present invention will be described in more detail with reference to the non-limitative examples.

EXAMPLE 1

(Preparation of copper oxide catalyst)

20% by weight of aqueous solution of sodium carbonate was added to 20% by weight of aqueous solution of copper sulfate until the mixture reaches pH 9 to 10 to deposit basic crystal of copper carbonate, which was filtered and washed repeatedly, dried in the stream of air at 130° C. and then calcined at 300° C. to produce copper oxide.

The copper oxide thus obtained was mixed with alumina sol (produced by Catalyst and Chemicals Industries Co., Ltd. under the tradename of Cataloid-AS-2) and the mixture was kneaded with a kneader. After drying in air at 130° C. the kneaded product was calcined at 350° C. and the calcined product was crushed to granule, which was formed into cylindrical pellets of 6 mm in diameter by 4 mm in height by means of tabletting forming. The tablets thus obtained were crushed and sieved to collect the powders of 6 to 12 mesh, which were packed in a purification cylinder made of stainless steel having an inside diameter of 16.4 mm and a length of 400 mm in a volume of 63 ml (101 g in weight, 1.6 g/ml in packing density, 300 mm in packing length). (Activation treatment of copper catalyst)

Hydrogen gas of 10 vol % in nitrogen was passed through the purification cylinder at 180° C., atmospheric pressure and a flow rate of 0.633 l/min (LV=5 cm/sec) for 6 hours to perform reduction treatment, followed by cooling to ordinary temperature.
(Purification of diethylzinc)

Subsequently diethylzinc was purified in the following manner.

In a thermostat set at 10° C. was immersed a stainless-steel made bubbler of 50 mm in diameter and 175 mm in height containing about 50 ml of diethylzinc. By adjusting the vapor pressure of diethylzinc in the above way and bubbling it with nitrogen, 1.2 vol % diethylzinc gas in nitrogen was generated. The oxygen concentration in the gas was measured with a white-phosphorus emission oxygen analyzer with a lowest measurable concentration of 0.01 ppm. The result was about 0.3 ppm.

The gas was passed through the purification cylinder at a flow rate of 0,633 l/min (LV=5 cm/sec) and the gas at the outlet thereof was analyzed for oxygen concentration. The result was not higher than 0.01 ppm, which was maintained for 100 minutes after the beginning of the gas purification.

EXAMPLE 2

(Purification of trimethylgallium)

By the use of the same purification cylinder that was used in Example 1 trimethylgallium was purified in the following manner.

In a thermostat set at 10° C. was immersed a stainless-steel made bubbler of 50 mm in inside diameter and 175 mm in height containing about 50 ml of trimethylgallium. By adjusting the vapor pressure of trimethylgallium in the above way and bubbling it with nitrogen, 5 vol % trimethylgallium gas in nitrogen was generated. The oxygen concentration in the gas was measured with a white-phosphorus emission type oxygen analyzer. The result was about 0.15 ppm.

The gas was passed through the purification cylinder at a flow rate of 0.633 l/min (LV=5 cm/sec) and the gas at the outlet thereof was analyzed for oxygen concentration. The result was not higher than 0.01 ppm, which was maintained for at least 100 minutes after the beginning of the gas purification.

EXAMPLE 3

(Purification of trimethylaluminum)

By the use of the same purification cylinder that was used in Example 1 trimethylaluminum was purified in the following manner.

In a thermostat set at 20° C. was immersed a stainless-steel made bubbler of 50 mm in inside diameter and 175 mm in height containing about 75 ml of trimethylaluminum. By adjusting the vapor pressure of the trimethylaluminum in the above way and bubbling it with nitrogen, 1.2 vol % trimethylaluminum gas in nitrogen was generated. The oxygen concentration in the gas was measured with a white-phosphorus emission type oxygen analyzer. The result was about 0.35 ppm.

The gas was passed through the purification cylinder at a flow rate of 0.663 l/min (LV=5 cm/sec) and the gas at the outlet thereof was analyzed for oxygen concentration. The result was not higher than 0.01 ppm, which was maintained for at least 100 minutes after the beginning of gas purification.

EXAMPLE 4

(Preparation of copper oxide catalyst)

There was used a commercially available copper oxide catalyst (produced by Nissan Girdler Co., Ltd. under the tradename of G 108) which was deposited on $SiO_2$ as the carrier containing 30% by weight of Cu component and having a specific surface area of 120 m²/g, diameter of 5 mm and height of 4.5 mm. The catalyst was crushed to 8 to 10 mesh, and the crushed product was packed in a purification cylinder made of stainless steel having an inside diameter of 16.4 mm and a length of 400 mm in a volume of 63 ml at a packing length of 300 mm and a packing density of 1.0 g/ml.
(Reducing treatment of catalyst)

Hydrogen gas of 10 vol % in nitrogen was passed through the cylinder at 180° C., atmospheric pressure and a flow rate of 0.633 l/min (LV=5 cm/sec) for 6 hours to perform reduction treatment, followed by cooling to ordinary temperature.

(Purification of diethylzinc)

Subsequently diethylzinc was purified in the following manner:

The 1.2 vol % diethylzinc gas in nitrogen containing about 0.3 ppm oxygen as used in Example 1 was passed through the purification cylinder at a flow rate of 0,633 l/min (LV=5 cm/sec) and the gas at the outlet thereof was analyzed for oxygen concentration. The result was not higher than 0.01 ppm, which was maintained for at least 100 minutes after the beginning of gas purification.

EXAMPLE 5

(Purification of trimethylgallium)

By the use of the same purification cylinder that was used in Example 4 trimethylgallium was purified in the following manner:

The 5 vol % trimethylgallium gas in nitrogen containing about 0.15 ppm oxygen as used in Example 2 was passed through the purification cylinder at a flow rate of 0.633 l/min (LV=5 cm/sec) and the gas at the outlet thereof was analyzed for oxygen concentration. The result was not higher than 0.01 ppm, which was maintained for at least 100 minutes after the beginning of gas purification.

EXAMPLE 6

(Purification of trimethylaluminum)

By the use of the same purification cylinder as used in Example 4 trimethylaluminum was purified in the following manner:

The 1.2 vol % trimethylaluminum gas in nitrogen containing about 0.35 ppm oxygen as used in Example 3 was passed through the purificaiton cylinder at a flow rate of 0.633 l/min (LV=5 cm/sec) and the gas at the outlet thereof was analyzed for oxygen concentration. The result was not higher than 0.01 ppm, which was maintained for at least 100 minutes after the beginning of gas purification.

EXAMPLE 7

(Preparation of nickel catalyst)

There was used a commercially available molded nickel catalyst in the form of Ni+NiO (produced by JGC Corporation under the tradename of N-111) containing 45 to 47 wt % Ni, 2 to 3 wt % Cr, 2 to 3 wt % Cu, 27 to 29 wt % diatomaceous earth and 4 to 5% graphite and having a specific surface area of 150 $m^2/g$, diameter of 5 mm and height of 4.5 mm. The catalyst was crushed to 8 to 10 mesh, and the crushed product was packed in a stainless-steel made purification cylinder having an inside diameter of 16.4 mm and a length of 400 mm in a volume of 63 ml at a packing length of 300 mm and a packing density of 1.0 g/ml.

(Reducing treatment of nickel catalyst)

Hydrogen gas was passed through the cylinder at 150° C., atmospheric pressure and a flow rate of 0.456 l/min (LV=3.6 cm/sec) for 3 hours to effect reduction treatment, followed by cooling to ordinary temperature.

(Purification of diethylzinc)

Subsequently diethylzinc was purified in the following manner:

In a thermostat set at 10° C. was immersed a stainless-steel made bubbler of 50 mm in inside diameter and 175 mm in height containing about 50 ml of diethylzinc. By adjusting the vapor pressure of the diethylzinc in the above way and bubbling it with nitrogen, 1.2 vol % diethylzinc gas in nitrogen was generated. The oxygen concentration in the gas was measured with a white-phosphorus emission type oxygen analyzer with a lowest measurable concentration of 0.01 ppm. The result was about 0.3 ppm.

The gas was passed through the purification cylinder at a flow rate of 0.633 l/min (LV=5 cm/sec) and the gas at the outlet thereof was analyzed for oxygen concentration. The result was not higher than 0.01 ppm, which was maintained for at least 100 minutes after the beginning of gas purification.

EXAMPLE 8

(Purification of trimethylgallium)

By the use of the same purification cylinder that was used in Example 7 trimethylgallium was purified in the following manner:

In a thermostat set at −10° C. was immersed a stainless-steel made bubbler of 50 mm in inside diameter and 175 mm in height containing about 50 ml of trimethylgallium. By adjusting the vapor pressure of the trimethylgallium in the above way and bubbling it with nitrogen, 5 vol% trimethylgallium gas in nitrogen was generated. The oxygen concentration in the gas was measured with a white-phosphorus emission type oxygen analyzer. The result was about 0.15 ppm.

The gas was passed thought the purification cylinder at a flow rate of 0.663 l/min (LV=5 cm/sec) and the gas at the outlet thereof was analyzed for oxygen concentration. The result was not higher than 0.01 ppm, which was maintained for at least 100 minutes after the beginning of gas purification.

EXAMPLE 9

(Purification of trimethylaluminum)

By the use of the same purification cylinder that WAS used in Example 7 trimethylaluminum was purified in the following manner:

In a thermostat set at 20° C. was immersed a stainless-steel made bubbler of 50 mm in inside diameter and 175 mm in height containing about 75 ml of trimethylaluminum. By adjusting the vapor pressure of the trimethylaluminum in the above way and bubbling it with nitrogen, 1.2 vol % trimethylaluminum gas in nitrogen was generated. The oxygen concentration in the gas was measured with a white-phosphorus emission type oxygen analyzer. The result was about 0.35 ppm.

The gas was passed through the purification cylinder at a flow rate of 0.633 l/min (LV=5 cm/sec) and the gas at the outlet thereof was analyzed for oxygen concentration. The result was not higher than 0.01 ppm, which was maintained for at least 100 minutes after the beginning of gas purification.

EXAMPLE 10

$Al(NO_3)_3.9H_2O$ of 454 g was dissolved in 3 liters of water, the resultant solution was cooled on an ice bath to 5 to 10° C., and added dropwise to a solution of 200 g of NaOH in 1 liter of water with vigorous stirring over a period of 2 hours to produce sodium aluminate.

Subsequently $Ni(NO_3)_2.6H_2O$ of 101 g was dissolved in 600 ml of water, and the resultant solution was incorporated with 45 ml of concentrated sulfuric acid and cooled to 5° to 10° C. The cooled mixture was added dropwise to the solution of sodium aluminate with vigorous stirring over a period of one hour. The resultant precipitate was filtered and the filter cake was washed 6 times repeatedly each by mixing with 2 liters of water for 15 minutes to obtain a neutral cake, which was divided into small pieces, dried in an air bath at 105° C. for 16 hours, crushed and sieved to collect the powders of 12 to 24 mesh. The resultant powders contained 29.5 wt % of NiO.

(Reducing treatment of nickel catalyst)

The catalyst thus obtained was packed in the same purification cylinder as used in Example 7 in an amount of 63 ml at a packing density of 0.77 g/ml and then hydrogen was passed through the cylinder at 350° C., ordinary pressure and a flow rate of 0.127 l/min (LV=i cm/sec) for 16 hours to perform reduction treatment, followed by cooling to ordinary temperature.

(Purification of diethylzinc)

Subsequently diethylzinc was purified in the following manner:

The 1.2 vol % diethylzinc gas in nitrogen containing about 0.3 ppm oxygen as used in Example 7 was passed though the purification cylinder at a flow rate of 0,633 l/min (LV=5 cm/sec) and the gas at the outlet thereof was analyzed for oxygen concentration. The result was not higher than 0.01 ppm, which was maintained for at least 100 minutes after the beginning of gas purification.

EXAMPLE 11

(Purification of trimethylgallium)

By the use of as the same purification cylinder as used in Example 10 trimethylgallium was purified in the following manner:

The 5 vol % trimethylgallium gas in nitrogen containing about 0.15 ppm oxygen as used in Example 10 was passed through the purification cylinder at a flow rate of 0,633 l/min (LV=5 cm/sec) and the gas at the outlet thereof was analyzed for oxygen concentration. The result was not higher than 0.01 ppm, which was maintained for at least 100 minutes after the beginning of gas purification.

EXAMPLE 12

(Purification of trimethylaluminum)

By the use of the same purificaiton cylinder that was used in Example 10 trimethylaluminum was purified in the following manner:

The 1.2 vol % trimethylaluminum gas in nitrogen containing about 0.35 ppm oxygen as used in Example 10 was passed through the purification cylinder at a flow rate of 0.633 l/min (LV=5 cm/sec) and the gas at the outlet thereof was analyzed for oxygen concentration. The result was not higher than 0.01 ppm, which was maintained for at lest 100 minutes after the beginning of gas purification.

Comparative Example 1

Coconut shell-based activated carbon crushed to 8 to 24 mesh in an amount of 48 g was packed in the same purificaiton cylinder that used in Example 1 at a packing length of 300 mm (packing density of 0.57 g/ml), and then helium gas was passed through the cylinder at 270° to 290° C. for heat treatment for hours, followed by cooling to room temperature.

The 1.2 vol % diethylzinc gas in nitrogen containing about 0.3 ppm oxygen as used in Example 1 was passed through the cylinder at a flow rate of 0.633 l/min (LV=5 cm/sec) and the gas at the outlet thereof was analyzed for oxygen concentration. The result was 0.3 ppm, which remained unchanged for further 2 hours under the same purification conditions.

What is claimed is:

1. A process for purifying a gaseous organometallic compound containing impurities comprising removing oxygen contained therein as an impurity by bringing the gaseous organometallic compound which is at least one compound selected from the group consisting of dimethylzinc, diethylzinc, dimethylcadmium, diethylcadmium, dimethylmercury, trimethylaluminum, triethylaluminum, diisobutylaluminum hydride, trimethoxyaluminum, dimethylaluminum monochloride, trimethylgallium, triethylgallium, triethoxygallium, trimethylindium, triethylindium, dimethylgold acetylacetonato, bishexafluoro acetylacetonato copper, biscyclopentadienylmagnesium, tetramethyltin, trimethyl arsenic, trimethylphosphorous, dimethylselenium, diethylselenium, dimethyltellurium and pentacarbonyliron into contact with a catalyst consisting essentially of (i) a component selected from the group consisting of metallic copper, copper oxide activated by reduction with hydrogen, metallic nickel and nickel oxide activated by reduction with hydrogen, and (ii) a carrier on which the metallic component is supported, said component being in an amount of 20 to 95% by weight expressed in terms of metallic copper or metallic nickel, based on the total amount of the metallic component and the carrier, said catalyst having a specific surface area as measured by the BET method of 30 to 250 $m^2/g$ and said catalyst being activated under reducing conditions by hydrogen.

2. The process according to claim 1 wherein the gaseous organometallic compound is diluted with hydrogen or an inert gas.

3. The process according to claim 1 wherein oxygen as an impurity is removed to a concentration of 0.1 ppm or lower, 4. The process according to claim 1 further comprising a dehumidification step by the use of a dehumidifying agent.

5. The process according to claim 1, wherein the carrier on which the metallic nickel or nickel oxide activated by reduction with hydrogen is deposited is selected from the group consisting of diatomaceous earth, alumina, silica-alumina, aluminosilicate and calcium silicate.

6. The process according to claim 5, wherein the process is carried out at a linear space velocity of the organometallic compound of 100 cm/second or less.

7. The process according to claim 6 wherein the linear space velocity is 30 cm/second or less.

8. The process according to claim 7 wherein the process is carried out at a temperature which is not higher than 200° C.

9. The process according to claim 8 wherein the process is carried out at a pressure of 20 $kg/cm^2$ or lower.

10. The process according to claim 9 wherein the pressure is 0.1 to 10 $kg/cm^2$ absolute.

11. The process according to claim 1 wherein the component consists essentially of metallic copper or copper oxide activated by reduction with hydrogen.

12. The process according to claim 1 wherein the component consists essentially of metallic nickel or nickel oxide activated by reduction with hydrogen.

13. The process according to claim 1, wherein the carrier on which the metallic copper or copper oxide activated by reduction with hydrogen is deposited is selected from the group consisting of alumina and silica.

14. The process according to claim 13, wherein the process is carried out at a linear space velocity of the organometallic compound of 100 cm/second or less.

* * * * *